US011060962B2

(12) United States Patent
Kono et al.

(10) Patent No.: US 11,060,962 B2
(45) Date of Patent: Jul. 13, 2021

(54) FLOW ANALYSIS METHOD

(71) Applicant: HITACHI, LTD., Tokyo (JP)

(72) Inventors: Tsutomu Kono, Tokyo (JP); Ryotaro Shimada, Tokyo (JP); Tsubasa Watanabe, Tokyo (JP); Hiroki Nakatsuchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 323 days.

(21) Appl. No.: 16/094,375

(22) PCT Filed: Apr. 18, 2016

(86) PCT No.: PCT/JP2016/062230
§ 371 (c)(1),
(2) Date: Oct. 17, 2018

(87) PCT Pub. No.: WO2017/183075
PCT Pub. Date: Oct. 26, 2017

(65) Prior Publication Data
US 2019/0120739 A1    Apr. 25, 2019

(51) Int. Cl.
*G01N 11/00*    (2006.01)
*G06F 30/23*    (2020.01)
(Continued)

(52) U.S. Cl.
CPC ............. *G01N 11/00* (2013.01); *B29C 43/58* (2013.01); *B29C 45/7693* (2013.01);
(Continued)

(58) Field of Classification Search
CPC ................ G01N 11/00; G01N 33/442; G01N 2011/0093; G01N 2033/0095;
(Continued)

(56) References Cited

U.S. PATENT DOCUMENTS 6,305,906 B1    10/2001 Ekstrom
2010/0103977 A1*  4/2010 Kono ................ B29C 45/7693
374/57

FOREIGN PATENT DOCUMENTS

JP    2000-220653 A    8/2000
JP    2008-191830 A    8/2008
JP    2010-108150 A    5/2010

OTHER PUBLICATIONS

Dimian et al., Computer Aided Chemical Engineering, 2014, Elsevier B.V., vol. 35 (Year: 2014).*

(Continued)

*Primary Examiner* — Alessandro V Amari
*Assistant Examiner* — Christian T Bryant
(74) *Attorney, Agent, or Firm* — Volpe Koenig

(57) ABSTRACT

Provided is a flow analysis method capable of predicting a flow state of a composite resin material by taking into account a change in filler dispersion degree of the composite resin material. In a flow analysis method for a composite resin material having a filler and a resin, in a certain process of identifying a region in which the composite resin material flows and analyzing a flow, an exothermic reaction speed of the composite resin material in the region is computed using a filler dispersion degree in the composite resin material, a temperature and the filler dispersion degree of the composite resin material in the region is computed using the computed exothermic reaction speed, and an exothermic reaction speed in a process subsequent to a process is computed using the computed filler dispersion degree.

13 Claims, 11 Drawing Sheets (a) MOLDING (b) GATE CUTTING (c) DICING

(51) Int. Cl.
  *G06F 30/00* (2020.01)
  *G01F 1/696* (2006.01)
  *B29C 43/58* (2006.01)
  *G01N 33/44* (2006.01)
  *B29C 45/76* (2006.01)
  *G01N 33/00* (2006.01)
  *B29K 105/16* (2006.01)
  *B29C 45/14* (2006.01)
  *G06F 113/18* (2020.01)

(52) U.S. Cl.
  CPC ........... *G01F 1/696* (2013.01); *G01N 33/442* (2013.01); *G06F 30/00* (2020.01); *G06F 30/23* (2020.01); *B29C 45/14655* (2013.01); *B29K 2105/16* (2013.01); *G01N 2011/0093* (2013.01); *G01N 2033/0003* (2013.01); *G01N 2033/0095* (2013.01); *G06F 2113/18* (2020.01)

(58) Field of Classification Search
  CPC ...... G06F 30/23; G06F 30/00; G06F 2113/18; B29C 43/58; B29C 45/7693; B29C 45/14655; G01F 1/696; B29K 2105/16
  See application file for complete search history.

(56) References Cited

OTHER PUBLICATIONS

Tam et al., Advances in Military Textiles and Personal Equipment, 2012, Woodhead Publishing, Chapter 10 (Year: 2012).*
Messaadi et al., "A New Equation Relating the Viscosity Arrhenius Temperature and the Activation Energy for Some Newtonian Classical Solvents", May 2015, Journal of Chemistry, vol. 2015 (Year: 2015).*
International Search Report dated Jun. 7, 2016 for the International Application No. PCT/JP2016/062230.

* cited by examiner (a) MOLDING (b) GATE CUTTING (c) DICING (a) MOLDING (b) BALL MOUNTING (c) DICING

FIG. 3

| FILLER DISPERSION DEGREE | EXOTHERMIC REACTION SPEED (W/kg) | THERMAL CONDUCTIVITY (W/m/K) |
|---|---|---|
| DENSE | AMOUNT OF RESIN DECREASES ⇒ CALORIFIC VALUE (SMALL) | AMOUNT OF RESIN DECREASES ⇒ THERMAL CONDUCTIVITY (LARGE) |
| SPARSE | AMOUNT OF RESIN INCREASES ⇒ CALORIFIC VALUE (LARGE) | AMOUNT OF RESIN INCREASES ⇒ THERMAL CONDUCTIVITY (SMALL) |

F I G. 6
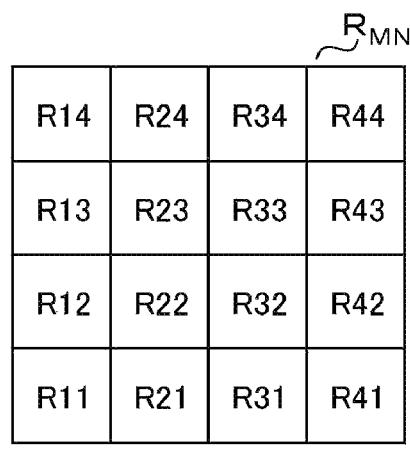

FIG. 11

TABLE 1

| PHYSICAL PROPERTY | RESIN (EPOXY) | FILLER (SILICA) |
|---|---|---|
| THERMAL CONDUCTIVITY | 0.2(W/m/K) | 10(W/m/K) |
| LINEAR EXPANSION COEFFICIENT | 30(ppm/°C) | 0.55(ppm/°C) |
| DENSITY | 1100(kg/m$^3$) | 2200(kg/m$^3$) |

FIG. 12

TABLE 2

| ka1 | ka2 | kb | Ea | Eb | M | N | Qr | Qr1 | Qr2 |
|---|---|---|---|---|---|---|---|---|---|
| 1.00E+34 | −2.30E+01 | 3.00E+03 | 2.98E+04 | 3.00E+04 | 1.00E+00 | 4.96E+00 | 2.74E+05 | −2.72E+05 | 2.75E+05 |

F I G. 1 3

TABLE 3

| F | G | D | E | Agel | T | n |
|---|---|---|---|------|---|---|
| 2.00E−05 | 4.58E+03 | 3.60E+00 | 1.87E+00 | 6.00E−01 | 1.00E+00 | 1.00E+00 |

FLOW ANALYSIS METHOD

TECHNICAL FIELD

The present invention relates to a flow analysis method and system for a composite resin material containing a resin component and a filler, and particularly relates to flow analysis reflecting a change in filler dispersion degree due to a flow in a resin molding process.

BACKGROUND ART

For example, a composite resin material obtained by mixing a filler and a resin has been widely used for producing a semiconductor package, etc. As a representative production method of a semiconductor package, a transfer molding method and a compression molding method have been known. In either production method, the semiconductor package is formed by filling a space between molds holding an element with a resin component while causing the resin component to flow.

In the semiconductor package, Package on Package (hereinafter "PonP") and a stack structure are used to cope with thinning and miniaturization of electronic equipment such as a mobile phone in recent years, and a gap allowing resin to flow during production is further miniaturized. When the composite resin material is caused to flow through such a minute space, an influence of a variation in dispersion degree of a filler contained in the composite resin material becomes a problem. For example, Patent Document 1 discloses a method of casting a resin molded body in which a difference in segregation state of a filler between respective molding dies of curing agent-mixed resin to be conveyed into a heat curing furnace is eliminated by circulating a process of injecting a curable resin into a preheating molding die, a process of thermally curing the injected resin, and a process of releasing a cured body and performing setup of tooling of a molding die in this order at a predetermined time difference using a plurality of molding dies.

CITATION LIST

Patent Document

Patent Document 1: JP 2000-220653 A

SUMMARY OF THE INVENTION

Problems to be Solved by the Invention

As described above, when the composite resin material is caused to flow through the minute space between the molds holding the element, a part of the filler contained in the composite resin material is likely to come into contact with the element on an upstream side in a flow direction and remain. For this reason, as the composite resin material flows, the filler dispersion degree becomes dense and sparse. In this case, due to heat generated at the time of crosslinking of the resin contained in the composite resin material or a difference in thermal conductivity between the resin and the filler, a difference occurs in an exothermic reaction speed or thermal conductivity in the composite resin material depending on the denseness/sparseness of the filler dispersion degree. As a result, a time difference occurs in the degree of crosslinking between molecules of the resin component, and a difference in viscosity occurs in the composite resin material, so that a flow behavior thereof becomes nonuniform. For this reason, there is a possibility of occurrence of a poor filling such as a case in which some regions are not filled with the composite resin material.

Patent Document 1 fails to disclose a relation between the filler dispersion degree in the composite resin material and the flow behavior of the composite resin material. For this reason, at present, a condition capable of suppressing poor filling of the composite resin material is selected by repeating prototyping of a product with regard to a composition of the composite resin material such as a structure, a process condition, a filler filling rate, etc., and it takes time and effort to determine an appropriate condition.

Therefore, an object of the invention is to provide a flow analysis method and system capable of predicting a flow state of a composite resin material by taking into account a change in filler dispersion degree of the composite resin material.

Solutions to Problems

As a preferred embodiment of a flow analysis method according to the invention, a flow analysis method for a composite resin material having a filler and a resin includes identifying a region in which the composite resin material flows, and computing an exothermic reaction speed of the composite resin material in the region using a filler dispersion degree in the composite resin material, computing a temperature and a filler dispersion degree of the composite resin material in the region using the computed exothermic reaction speed, and computing an exothermic reaction speed in a process subsequent to a certain process for flow analysis using the computed filler dispersion degree in the process for flow analysis.

As a preferred embodiment of a flow analysis system according to the invention, a flow analysis system for performing flow analysis of a composite resin material having a filler and a resin includes a calculation device that computes an exothermic reaction speed of the composite resin material using a filler dispersion degree, computes a temperature, a filler dispersion degree, and a flow velocity of the composite resin material in a certain region specified as a region in which the composite resin material flows using the computed exothermic reaction speed, and computes an exothermic reaction speed in a process subsequent to a process for flow analysis using the computed filler dispersion degree and temperature in the process for flow analysis in the region specified as the region in which the composite resin material flows according to execution of a program, a storage device that stores data related to the temperature and the filler dispersion degree of the composite resin material computed by the calculation device, and a display device that displays data related to the flow velocity of the composite resin material computed by the calculation device.

Effects of the Invention

According to the invention, it is possible to predict a flow state of a composite resin material by taking into account a change in filler dispersion degree of the composite resin material.

BRIEF DESCRIPTION OF THE DRAWINGS

FIG. 3 is a diagram showing denseness/sparseness of a filler dispersion degree and a magnitude relation of an exothermic reaction speed and thermal conductivity.

FIG. 6 is a diagram illustrating divided regions of the flow analysis method according to the embodiment.

FIG. 11 is a diagram showing Table 1.

FIG. 12 is a diagram showing Table 2.

FIG. 13 is a diagram showing Table 3.

MODE FOR CARRYING OUT THE INVENTION

Hereinafter, an embodiment according to the invention will be described with reference to accompanying drawings.

Figure 1:
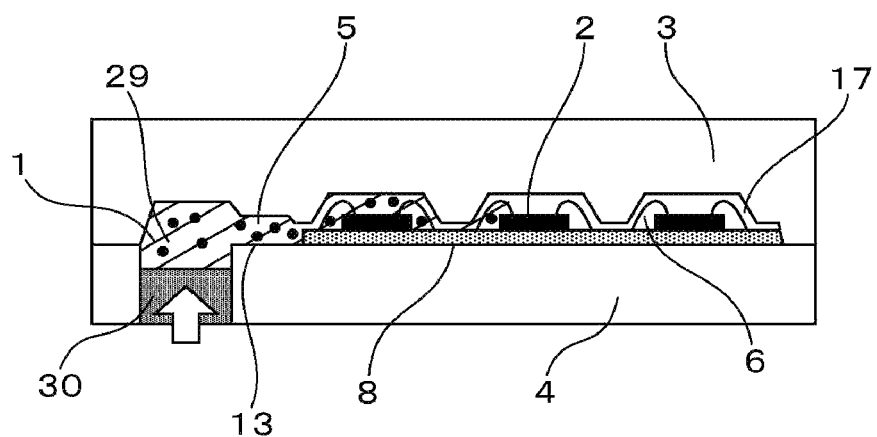
FIG. 1 is a diagram for describing a method of forming a semiconductor package by a transfer molding method.
Figure 1:
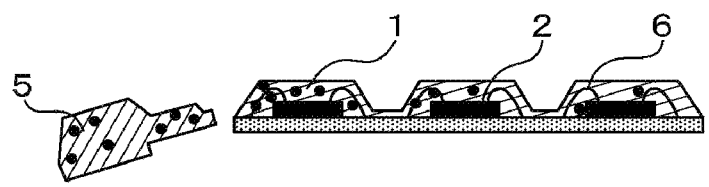
Figure 1:
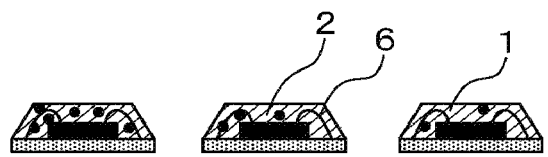
Figure 2:
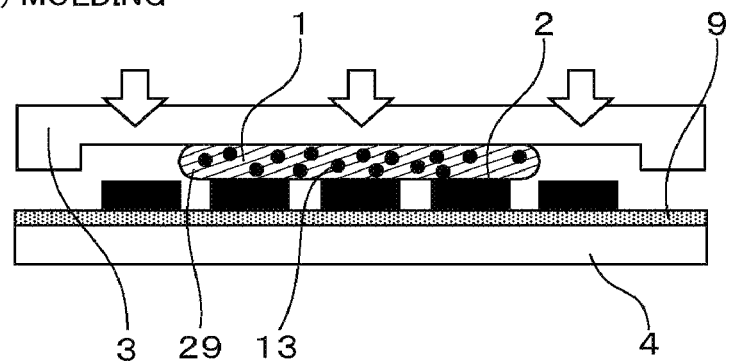
FIG. 2 is a diagram for describing a method of forming a semiconductor package by a compression molding method.
Figure 2:
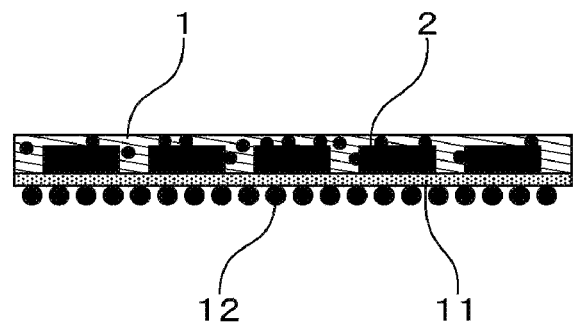
Figure 2:
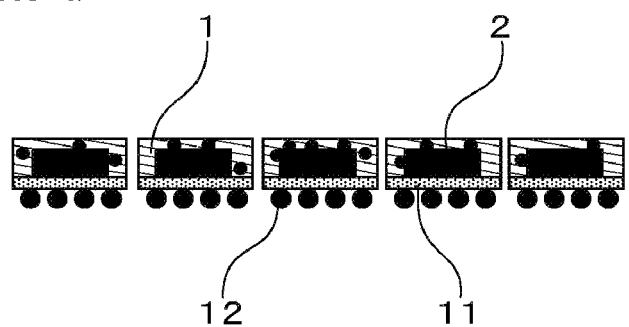

First, representative molding methods of a semiconductor package to which a flow analysis method according to an embodiment is applied are illustrated in FIG. 1 and FIG. 2.

FIG. 1 is a diagram for describing a method of forming a semiconductor package by a transfer molding method. In transfer molding, as illustrated in FIG. 1(a), a lead frame 8 on which an element 2 is mounted by a gold wire 6 is clamped by an upper mold 3 and a lower mold 4, and a space 17 in a gap between the upper mold 3 and the lower mold 4 is filled with a composite resin material 1. The composite resin material 1 is a mixture in which a filler 13 is added to a resin 29.

After solidification of the composite resin material 1, a gate, cull 5, which is a resin flow path part outside a product of the semiconductor package, is cut (see FIG. 1(b)), and the semiconductor package is further diced by dicing (see FIG. 1(c)).

FIG. 2 is a diagram for describing a method of forming a semiconductor package by a compression molding method. In the compression molding method, first, a fixing film 9 on which the element 2 is mounted is installed on the lower mold 4, and the composite resin material 1 is placed on the element 2 and the fixing film 9. Thereafter, by heating and pressurizing the composite resin material 1 using the upper mold 3, a space between the upper mold 3 and the lower mold 4 is filled with the composite resin material 1 while the composite resin material 1 is caused to flow.

After solidification of the composite resin material 1, the fixing film 9 is peeled off from the element 2, a rewiring layer 11 is installed to install a solder ball 12, etc. for inputting/outputting an electric signal (see FIG. 2(b)), and the semiconductor package is divided into individual pieces by dicing (see FIG. 2(c)).

For example, in a case in which a crosslinkable resin that crosslinks due to heat generation is used as a resin 29 contained in the composite resin material 1, when the composite resin material 1 is heated, a crosslinking reaction between molecules of the resin 29 further progresses in response to heat generation of the resin 29 due to the crosslinking reaction. As a result, the viscosity of the composite resin material 1 rises, and the composite resin material 1 finally cures to a solid state.

In the transfer molding method illustrated in FIG. 1, specifically, the composite resin material 1 is injected into the space 17 from the gate or cull 5 and flows. In this instance, a large amount of the filler 13 is dispersed in the vicinity of the element 2 on the gate, cull 5 side, which is the upstream side of the composite resin material 1 in a flow direction. On the other hand, a small amount of the filler 13 is dispersed in the vicinity of the element 2 located on a downstream side of the composite resin material 1 in the flow direction, that is, on an opposite side from the gate, cull 5.

FIG. 3 shows denseness/sparseness of the filler dispersion degree and a magnitude relation of the exothermic reaction speed and the thermal conductivity. In addition, Table 1 (see FIG. 11) shows values of thermal conductivity, linear expansion coefficient, and density for epoxy resin as the resin 29 and silica as the filler 13. Here, the filler dispersion degree represents a volume ratio of the filler 13 contained in the composite resin material 1. In addition, the exothermic reaction speed represents a temporal change in calorific value per unit volume of the composite resin material 1.

As shown in FIG. 3, when the filler dispersion degree is low (when the filler is sparse), a volume ratio of resin contributing to the exothermic reaction is high, and thus the exothermic reaction speed as the composite resin material 1 increases. On the other hand, when the filler dispersion degree is high (when the filler is dense), as shown in FIG. 3 and Table 1, the dispersion degree of the filler 13 having higher thermal conductivity than that of the resin 29 is high, and thus the thermal conductivity of the composite resin material 1 increases.

Figure 4:
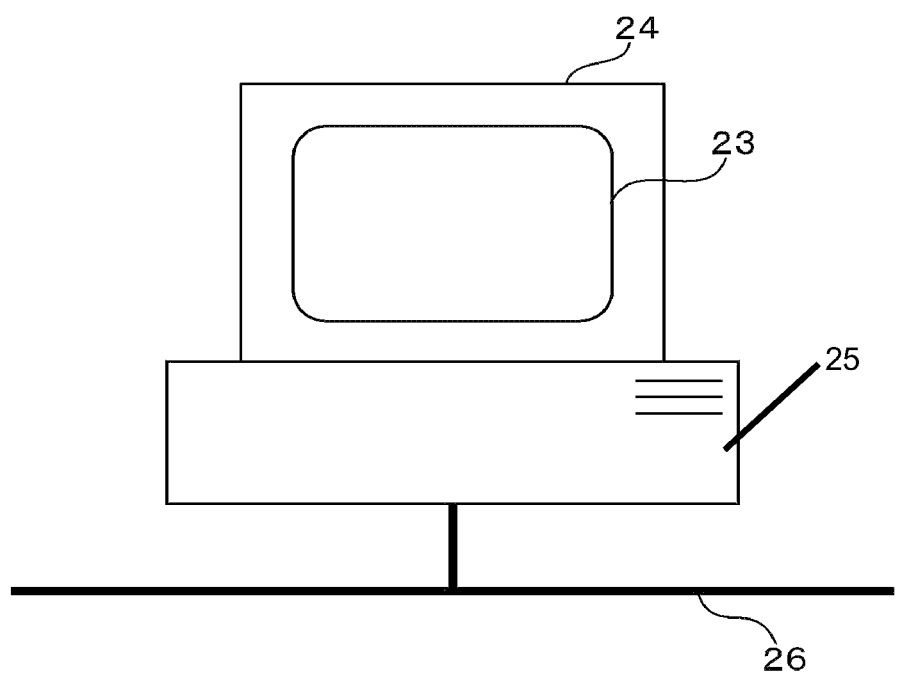
FIG. 4 is a diagram illustrating a hardware configuration of an analysis system used for flow analysis according to an embodiment.
Figure 5:
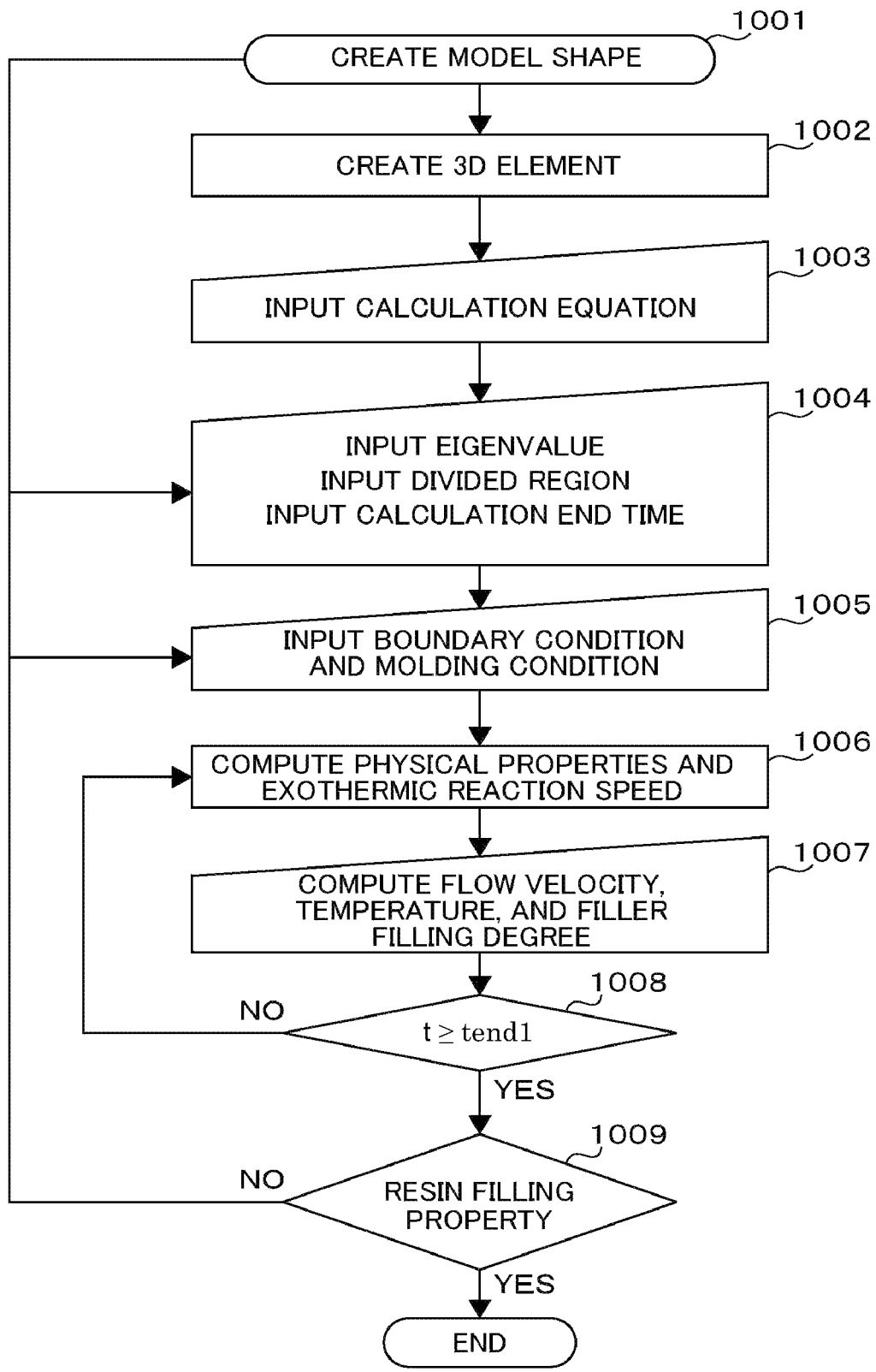
FIG. 5 is a flowchart illustrating processing processes of a flow analysis method according to the embodiment.

FIG. 4 is a hardware configuration of an analysis system used for flow analysis according to the embodiment, and functions by executing a process according to a flowchart of FIG. 5 by a program. Specifically, the hardware configuration includes a calculation device 24 including a storage device 25 such as a hard disk, a DVD, etc., a LAN 26 connecting other devices, and a display device 23. The calculation device 24 executes calculation according to the flowchart illustrated in FIG. 5. A calculation result is stored in the storage device and displayed on the display device 23. Although not illustrated, the calculation device 24 includes an input device such as a keyboard, a mouse, etc.

Next, the flow analysis method for the composite resin material 1 according to the embodiment will be described with reference to the flowchart of FIG. 5.

In description below, it is presumed that a resin which crosslinks or polymerizes with the exothermic reaction is used as the resin 29 contained in the composite resin material 1. Specifically, for example, it is sufficient to contain a component such as an epoxy resin, an unsaturated polyester resin, a polyurethane resin, etc., which cause a polymerization reaction of monomers accompanied by an exothermic reaction or crosslinking of polymers. The composite resin material 1 may contain a thermoplastic resin, etc. not accompanied by the exothermic reaction.

As the filler 13 contained in the composite resin material 1, for example, it is possible to use an inorganic filler containing a component such as silica, mica, talc, etc., an organic filler containing a component such as a polymer material, and a metal filler containing a component such as copper, aluminum, gold, silver, etc.

The flow analysis method described below is to calculate a change state of a temperature or flow velocity during flowing of the composite resin material 1 whose viscosity varies with an exothermic reaction by reflecting a change predicted value of the filler dispersion degree. That is, the flow analysis method described below is characterized by computing the exothermic reaction speed using exothermic reaction speed equations (Equation 1) to (Equation 8) including the filler dispersion degree as an input term, and computing the flow velocity and temperature of the composite resin material using computed values thereof.

(Step 1001)

First, in step 1001, an analysis target model is input as shape data to the storage device 25 by an operator through an input device (not illustrated) (model shape creation step 1001). For example, the analysis target model corresponds to shape data including the space 17 (see FIG. 1) between the upper mold 3 and the lower mold 4, which is a flowing space of the composite resin material 1.

The analysis target model may be directly input to the storage device 25 by the input device, or CAD data created by another calculation device, etc. may be transferred to the calculation device 24 via the LAN 26 and stored in the storage device 25.

(Step 1002)

In step 1002, the calculation device 24 reads the shape data of the analysis target model input in step 1001 from the storage device 25, decomposes the shape data into finite elements such as three-dimensional (3D) solids as a plurality of specific spaces, and creates shape data of each of the finite elements (element creation step 1002).

(Step 1003)

Subsequently, in step 1003, exothermic reaction speed equations (Equation 1) to (Equation 8), viscosity equations (Equation 9) to (Equation 11), a density equation (Equation 12), a specific heat equation (Equation 13), and a thermal conductivity equation (Equation 14) of the composite resin material 1 having a filler dispersion degree Vwf as an input term shown below are input to the storage device 25 by the input device (not illustrated) (calculation equation input step 1003).

[Formula 1]
$$dA/dt = (K_1 + K_2 \cdot A^M)(1-A)^N \tag{1}$$

[Formula 2]
$$K_1 = K_a \cdot \exp(-Ea/t) \tag{2}$$

[Formula 3]
$$K_2 = K_b \cdot \exp(-Eb/t) \tag{3}$$

[Formula 4]
$$Ka = K_{a1} \cdot \text{EXP}(K_{a2} \cdot Vwf) \tag{4}$$

[Formula 5]
$$Q_0 = Vwr \cdot Qr - Vwf \cdot Qf \tag{5}$$

[Formula 6]
$$Qf = Q_{r1} \cdot Vwf + Q_{r2} \tag{6}$$

[Formula 7]
$$A = Q/Q_0 \tag{7}$$

[Formula 8]
$$dQ/dt = Q_0(K_1 + K_2 A^M)(1-A)^N \tag{8}$$

[Formula 9]
$$\eta = \eta_m (Agel/Agel-A)^{(D-EA)} \tag{9}$$

[Formula 10]
$$\eta_m = \eta_0/((1+(\eta_0 \gamma/\tau)^{(1-n)}) \tag{10}$$

[Formula 11]
$$\eta_0 = F \cdot \exp(G/T) \tag{11}$$

[Formula 12]
$$\rho = \rho f \cdot Vwf + \rho r \cdot Vwr \tag{12}$$

[Formula 13]
$$Cp = Cpf \cdot Vwf + Cpr \cdot Vwr \tag{13}$$

[Formula 14]
$$\lambda = \lambda f \cdot Vwf + \lambda r \cdot Vwr \tag{14}$$

Symbols in the above-mentioned (Equation 1) to (Equation 14) denote the following values, respectively.

A: reaction rate, t: time, T: temperature of composite resin material, dA/dt: reaction speed, $K_1$, $K_2$: coefficients corresponding to function of temperature, Ka: coefficient corresponding to function of filler dispersion degree, N, M, $K_{a1}$, $K_{a2}$, Ea, Kb, Eb, $Q_{r1}$, $Q_{r2}$: coefficients inherent to materials, Q: calorific value up to arbitrary time, $Q_0$: total calorific value up to end of reaction, Qr: total calorific value of resin excluding filler, Gf: heat quantity for raising temperature of filler, Vwf: filler dispersion degree (volume ratio of filler in composite resin material), Vwr: volume ratio of resin in composite resin material 1, dQ/dt: exothermic reaction rate, η: viscosity, Agel: reaction rate at gelation, $\eta_0$: initial viscosity, γ: shear velocity, τ, D, E, n, F, G: coefficients inherent to materials, ρ: density of composite resin material, ρf: density of filler in composite resin material, ρr: density of resin in composite resin material, Cp: specific heat of composite resin material, Cpf: specific heat of filler in composite resin material, Cpr: specific heat of resin in composite resin material, λ: thermal conductivity of composite resin material, λf: thermal conductivity of filler in composite resin material, λr: thermal conductivity of resin in composite resin material.

Note that γ of (Equation 10) is a shear velocity of the composite resin material 1, and is a value computed by velocities u, υ, and ω of (Equation 15) to (Equation 19) described below.

The temperature T and the reaction rate A of the resin computed by the exothermic reaction speed equations (Equation 1) to (Equation 8) having the filler dispersion degree Vwf as an input term are input to input terms of the temperature T and the reaction rate A of the resin of the viscosity equations (Equation 9) to (Equation 11). In addition, the density ρ, the thermal conductivity λ, and the specific heat Cp corresponding to physical properties of the composite resin material 1 may be computed as compound rules of the filler 13 and the resin 29 using the filler dispersion degree Vwf as shown in (Equation 12) to (Equation 14).

Input operations of (Equation 1) to (Equation 14) may not be performed, and equations stored in the storage device 25 in advance may be used.

(Step 1004)

Subsequently, in step 1004, an eigenvalues specified by a type of the composite resin material or a constituent material thereof in the above (Equation 1) to (Equation 14) is input to the storage device 25 by the input device (not illustrated) (eigenvalue input step 1004).

In step 1004, for example, a display prompting input of the eigenvalue may be displayed on the display device 23 by a graphical user interface (GUI), etc. and the operator may input various eigenvalues to the storage device 25 through the input device according to this display.

Specifically, for example, the eigenvalues correspond to coefficients N, M, $K_{a1}$, $K_{a2}$, Ea, Kb, Eb, $Q_{r1}$, $Q_{r2}$, and Qr of the exothermic reaction speed equations (Equation 1) to (Equation 8), the coefficients $\tau$, D, E, n, F, G, and Agel of the viscosity equations (Equation 9) to (Equation 11), the density $\rho$, the specific heat Cp, and the thermal conductivity $\lambda$ of each of the resin 29 and the filler 13, and the dispersion degree Vwf of the filler 13 in an initial state.

The filler dispersion degree Vwf is calculated as a ratio of the filler volume in the unit volume of the composite resin material 1. The filler volume is a total value of the volumes of a plurality of fillers contained in the unit volume of the composite resin material 1. Specifically, the filler volume can be calculated from a filler dimension or a filling ratio of the filler in the initial state of the composite resin material 1.

For this reason, for the filler 13, the filler dimension may be input to the storage device 25. For example, assuming that the fillers have spherical shapes, it is possible to input a distribution of diameters of spheres, etc. as the filler dimension.

For example, the coefficients of the exothermic reaction speed equations (Equation 1) to (Equation 8) and the coefficients of the viscosity equations (Equation 9) to (Equation 11) may not be input to the storage device 25 each time analysis processing is started, and it is possible to read and use a value previously stored in the storage device 25.

In step 1004, furthermore, in the shape data of the finite element created in step 1002, a divided region obtained by dividing a calculation target region subjected to calculation processing of (Equation 1) to (Equation 14) into a plurality of (two or more) regions is input to the storage device 25 by the input device (not illustrated). In step 1004, further, a calculation end time tend1 at which calculation processing ends is input to the storage device 25 by the input device (not illustrated).

The divided region may be the same region as the region of the finite element created in step 1002, or a region having a plurality of finite elements may be set as one divided region.

Hereinafter, as illustrated in FIG. 6, a case in which a space including elements obtained by dividing a region $R_{MN}$ subjected to calculation into 16 parts by setting M, N=1 to 4 is input as divided regions R11 to 14, R21 to 24, R31 to 34, and R41 to 44 will be described as an example. It is presumed that the plurality of divided regions is equal to the respective regions of the finite elements created in step 1002.

In a step to be described below, for example, in the case of obtaining a calculation result in which all regions in the space 17 are filled with the composite resin material 1 before the end time tend1 is reached, calculation processing may be set to end at this point in time.

(Step 1005)

Subsequently, in step 1005, a display prompting input of a boundary condition and a molding condition is displayed on the display device 23, and the boundary condition and the molding condition are input to the storage device 25 through the input device (not illustrated) by the operator according to this display (boundary condition/molding condition input step 1005).

Specifically, for example, the boundary condition and the molding condition correspond to an initial mold temperature, an initial temperature of the composite resin material 1, an initial velocity of the composite resin material 1, and an initial pressure of the composite resin material 1. The mold temperature corresponds to the temperature of the molds 3 and 4 and corresponds to a temperature of a contact portion of the composite resin material 1 with the molds 3 and 4 when the composite resin material 1 flows and comes into contact with the molds.

(Step 1006)

Subsequently, in step 1006 to step 1008, the calculation device 24 executes calculation processing. In step 1006 to step 1008 below, a case in which the composite resin material 1 flows in from an element R11 will be described as an example. In description below, step 1006 to step 1008 in which the exothermic reaction speed of the composite resin material in each divided region is computed using the filler dispersion degree Vwf, and the temperature and the filler dispersion degree Vwf of the composite resin material in each divided region are computed using the computed exothermic reaction speed are set as a series of calculation processes $t_n$ (n=1, 2, 3, ... ).

First, in an initial calculation process $t_1$, calculation processing is executed assuming that the composite resin material 1 flows from the divided region R11 into the divided regions R12, R22, and R21. In step 1006 of the calculation process $t_1$, the calculation device 24 reads the exothermic reaction speed equations (Equation 1) to (Equation 8), viscosity equations (Equation 9) to (Equation 11), the density equation (Equation 12), the specific heat equation (Equation 13), and the thermal conductivity equation (Equation 14) input in step 1003 from the storage device 25, substitutes the eigenvalue such as an initial filler dispersion degree input in step 1004 into (Equation 1) to (Equation 14) to execute calculation processing, and computes the physical properties (viscosity, density, thermal conductivity, and specific heat) and the exothermic reaction speed (dQ/dt) of the composite resin material 1 in each divided region (physical property/exothermic reaction speed computation step 1006).

(Step 1007)

Subsequently, in step 1007, an instruction to start analysis and an initial time increment are input to the calculation device 24 by the operator through the input device (not illustrated). Based on this input information, the calculation device 24 reads a series of equations shown below (Equation 15), equations of motion (Navier-Stokes Equations) (Equations 16) to (Equation 18), and a thermal energy preservation equation (Equation 19) stored in the storage device 25.

[Formula 15]

$$\frac{\partial \rho}{\partial t} + \frac{\partial (\rho u)}{\partial x} + \frac{\partial (\rho v)}{\partial y} + \frac{\partial (\rho \omega)}{\partial z} = 0 \qquad (15)$$

-continued

[Formula 16]

$$\rho\frac{\partial u}{\partial t} = \rho g_x - \frac{\partial P}{\partial x} + \frac{\partial}{\partial x}\left(2\eta\frac{\partial u}{\partial x}\right) + \frac{\partial}{\partial y}\left(\eta\left(\frac{\partial v}{\partial x} + \frac{\partial u}{\partial y}\right)\right) + \frac{\partial}{\partial z}\left(\eta\left(\frac{\partial u}{\partial z} + \frac{\partial \omega}{\partial x}\right)\right) - \rho\left(u\frac{\partial u}{\partial x} + v\frac{\partial u}{\partial y} + \omega\frac{\partial u}{\partial z}\right) \quad (16)$$

[Formula 17]

$$\rho\frac{\partial v}{\partial t} = \rho g_y - \frac{\partial P}{\partial y} + \frac{\partial}{\partial y}\left(2\eta\frac{\partial v}{\partial y}\right) + \frac{\partial}{\partial x}\left(\eta\left(\frac{\partial u}{\partial y} + \frac{\partial v}{\partial x}\right)\right) + \frac{\partial}{\partial z}\left(\eta\left(\frac{\partial \omega}{\partial y} + \frac{\partial v}{\partial z}\right)\right) - \rho\left(u\frac{\partial v}{\partial x} + v\frac{\partial v}{\partial y} + \omega\frac{\partial v}{\partial z}\right) \quad (17)$$

[Formula 18]

$$\rho\frac{\partial \omega}{\partial t} = \rho g_z - \frac{\partial P}{\partial z} + \frac{\partial}{\partial z}\left(2\eta\frac{\partial \omega}{\partial z}\right) + \frac{\partial}{\partial y}\left(\eta\left(\frac{\partial v}{\partial z} + \frac{\partial \omega}{\partial y}\right)\right) + \frac{\partial}{\partial x}\left(\eta\left(\frac{\partial u}{\partial z} + \frac{\partial \omega}{\partial x}\right)\right) - \rho\left(u\frac{\partial \omega}{\partial x} + v\frac{\partial \omega}{\partial y} + \omega\frac{\partial \omega}{\partial z}\right) \quad (18)$$

[Formula 19]

$$\rho Cp\left(\frac{\partial T}{\partial t} + u\frac{\partial T}{\partial x} + v\frac{\partial T}{\partial y} + \omega\frac{\partial T}{\partial z}\right) = \beta T\left(\frac{\partial P}{\partial t} + u\frac{\partial P}{\partial x} + v\frac{\partial P}{\partial y} + \omega\frac{\partial P}{\partial z}\right) + \eta\gamma^2 + \lambda\left(\frac{\partial^2 T}{\partial x^2} + \frac{\partial^2 T}{\partial y^2} + \frac{\partial^2 T}{\partial z^2}\right) + \rho\frac{\partial Q}{\partial t} \quad (19)$$

Symbols in the above-mentioned (Equation 15) to (Equation 19) denote the following values, respectively.

$\rho$: density, u: velocity in x direction, $\upsilon$: velocity in y direction, $\omega$: velocity in z direction, T: temperature, P: pressure, t: time, $\eta$: viscosity, Cp: specific heat, $\beta$: cubical expansion coefficient, $\lambda$: thermal conductivity, dQ/dt: exothermic reaction speed, acceleration of gravity g=9.807 m/s$^2$.

Subsequently, the calculation device 24 substitutes the physical properties (viscosity, density, thermal conductivity, and specific heat) and the exothermic reaction speed of the composite resin material 1 computed in the step 1006 into the above-mentioned (Equation 15) to (Equation 19), and executes calculation processing using the initial mold temperature, the initial temperature of the composite resin material 1, the initial velocity of the composite resin material 1, and the initial pressure of the composite resin material 1 input in step 1005 as the boundary condition and the molding condition. Through this calculation processing, contents including the flow velocity of the composite resin material 1 in the calculation process $t_1$, the pressure of the composite resin material 1, and the temperature of the composite resin material 1, accompanying the flow of the composite resin material 1 are computed for each divided region (flow state analysis step 1007).

Subsequently, the calculation device 24 performs calculation of computing the flow velocity for each of the resin 29 and the filler 13 using the viscosity equations (Equation 9) to (Equation 11), and computes the filler calculation process $t_1$ based on computation results of the flow velocity of the resin 29 and the flow velocity of the filler 13.

Here, a position of the filler 13 in the composite resin material 1 may be calculated by linking a flow behavior of the composite resin material 1 to a flow behavior of the filler 13 using the dimension or the density of the filler 13 input to the storage device 25 in step 1004. For example, after setting a virtual filler in the resin 29 and inputting density or a dimension of this filler to the storage device 25, the position of the filler 13 may be computed by computing the flow velocity of each of the resin 29 and the filler 13 associated with the flow of the composite resin material 1 using the density or the dimension of this filler. Alternatively, the position of the filler 13 may be computed by setting the filler 13 as an obstacle in the resin 29 and calculating a two-phase flow of the resin 29 and the filler 13. In addition, the filler 13 may be set in the composite resin material 1 using a marker, and calculation processing may be executed so that the filler 13 moves with the flow of the composite resin material 1.

In computation of the flow velocity for each of the resin 29 and the filler 13, it is possible to use at least one of the density obtained by the density equation (Equation 12), the specific heat obtained by the specific heat equation (Equation 13), and the thermal conductivity obtained by the thermal conductivity equation (Equation 14) in addition to the viscosity obtained by the viscosity equations (Equation 9) to (Equation 11).

In addition, when the filler 13 comes into contact with a boundary between an analysis target region and an external region, a mold wall surface, and a component, a friction coefficient with respect to the filler 13 may be set for the boundary, the mold wall surface, and the component. Further, in this instance, when the filler 13 comes into contact with the boundary with the external region, the mold wall surface, and the component, the filler 13 may be set to adhere to the boundary, the mold wall surface, and the component.

When the position of the filler 13 in the composite resin material 1 in each calculation process is computed as described above, it is possible to compute the filler dispersion degree Vwf in each calculation process.

The calculation device 24 saves an analysis result computed in step 1007 in the storage device 25 in association with a position of the finite element created in step 1002.

(Step 1008)

Subsequently, in step 1008, the calculation device 24 determines whether an elapsed time from a calculation start time of step 1007 has reached the calculation time tend1 set in step 1004. Then, when it is determined that tend1 has not been reached, the operation returns to step 1006 and calculation processing in a subsequent calculation process $t_2$ is executed.

In the calculation process $t_2$, resin filling from the divided region R11 is continued, and calculation processing is executed on the assumption that the composite resin material 1 flows into the divided regions R13, R23, R33, R32, and R31 in addition to the divided regions R11, R12, R22, and R21.

(Step 1006)

In step 1006 in the calculation process $t_2$, the calculation device 24 executes calculation processing by substituting the filler dispersion degree Vwf and the temperature T of the composite resin material 1 calculated in step 1007 of the calculation process $t_1$ into the input terms of the filler dispersion degree Vwf and the temperature T of the composite resin material 1 of the exothermic reaction speed equations (Equation 1) to (Equation 8), the viscosity equations (Equation 9) to (Equation 11), the density equation (Equation 12), the specific heat equation (Equation 13), and the thermal conductivity equation (Equation 14) and substituting the same numerical values as those substituted in step 1006 of the calculation process $t_1$ into input terms of the other eigenvalues, and computes the physical properties (viscosity, density, thermal conductivity, and specific heat)

and the exothermic reaction speed (dQ/dt) of the composite resin material 1 in the calculation process $t_2$.

Here, a method of computing the filler dispersion degree Vwf in each divided region when a composite resin material flows into one divided region from a plurality of divided regions will be described using a case in which the composite resin material 1 containing the resin 29 and the filler 13 flows into the divided region R23 from the divided region R12 and the divided region R22 as an example. In this case, the filler dispersion degree Vwf of the divided region R23 may be computed using ratios of inflow amounts of the resin 29 and the filler 13 from the divided region R12 and the divided region R22.

For example, when a volume ratio of the composite resin material 1 flowing from the divided region R12 into the divided region R23 out of the total volume of the composite resin material 1 flowing into the divided region R23 is set to V11, the filler dispersion degree of this composite resin material (the composite resin material 1 flowing from the divided region R12 into the divided region R23) is set to Vwf1, a volume ratio of the composite resin material 1 flowing from the divided region R22 into the divided region R23 out of the total volume of the composite resin material 1 flowing into the divided region 23 is set to V12, and the filler dispersion degree of this composite resin material (the composite resin material 1 flowing from the divided region R22 into the divided region R23) is set to Vwf2, a filler filling degree Vwf in the calculation process $t_2$ in the divided region 23 may be computed by Equation (20) below in step 1006.

[Formula 20]

$$Vwf = V11 \cdot Vwf1 + V12 \cdot Vwf2 \quad (20)$$

A formula for computing the filler dispersion degree Vwf in each divided region into which the composite resin material 1 flows from the plurality of divided regions is not limited to the above Equation (20). The filler dispersion degree Vwf may be computed from an inflow volume ratio and a filler filling degree of the composite resin material 1 for each divided region corresponding to an inflow source of the composite resin material 1 into one divided region.

In the above-mentioned example, a description has been given of a method of computing the filler dispersion degree in a case in which the composite resin material 1 flows into one divided region from two divided regions. However, referring to the filler dispersion degree, in a case in which the composite resin material 1 flows into one divided region from three divided regions, a filler filling degree of one divided region corresponding to an inflow destination may be similarly computed from an inflow volume ratio and a filler dispersion degree of the composite resin material 1 for each of three divided regions corresponding to inflow sources of the composite resin material 1 flowing into one divided region.

(Step 1007)

Subsequently, in step 1007 in the calculation process $t_2$, the calculation device 24 executes calculation processing similarly to step 1007 in the calculation process $t_1$ except that the physical properties (viscosity, density, thermal conductivity, and specific heat) and the exothermic reaction speed of the composite resin material 1 computed in step 1006 in the calculation process $t_2$ are substituted into the above (Equation 15) to (Equation 19), and computes contents including the flow velocity of the composite resin material 1 in the calculation process $t_2$, the pressure of the composite resin material 1, and the temperature of the composite resin material 1, accompanying the flow of the composite resin material 1.

Subsequently, the calculation device 24 performs calculation of computing a flow velocity for each of the resin 29 and the filler 13 similarly to step 1007 in the calculation process $t_1$, and computes the filler dispersion degree Vwf in each divided region based on a computation result thereof.

The calculation device 24 saves an analysis result computed in step 1007 in the storage device 25 in association with a position of the finite element created in step 1002.

(Step 1008)

Subsequently, in step 1008 in the calculation process $t_2$, the calculation device 24 determines whether an elapsed time from a calculation start time of step 1007 has reached the calculation time tend1. Then, when it is determined that tend1 has not been reached, the operation returns to step 1006 and calculation processing in a subsequent calculation process $t_3$ is started. Thereafter, the same calculation processing is repeated from step 1006 to step 1008 until the calculation time tend1 is reached.

(Step 1009)

When it is determined that the elapsed time from the calculation start time of step 1007 has reached the calculation time tend1, the calculation device 24 ends calculation processing.

Subsequently, the calculation device 24 evaluates a filling degree (resin filling property) of the composite resin material 1 in the entire calculation target region $R_{MN}$ at a calculation end time. For example, when it is determined that an unfilled region remains in a region to be filled with the composite resin material 1 at the calculation end time, the operation may return to step 1001 (model shape creation step 1001), step 1004 (eigenvalue input step 1004), and step 1005 (boundary condition/molding condition input step 1005), and analysis processing after step 1006 may be executed again by adjusting the model shape of the analysis target model, the eigenvalue specified by the type of the composite resin material or the constituent material thereof, the boundary condition, the molding condition, etc. so that the resin filling property is improved.

The calculation device 24 displays an analysis result such as the temperature, the filler dispersion degree, the flow velocity, etc. of the composite resin material for each calculation process computed by the calculation device 24 on the display device 23. The analysis result may be displayed in parallel with analysis processing or after the end of analysis processing.

The above description shows an example in which in step 1006, the filler dispersion degree Vwf computed in step 1007 of an immediately preceding calculation process $t_{n-1}$ is substituted into the input terms of (Equation 1) to (Equation 14) for each calculation process $t_n$, and the exothermic reaction speed and the physical property of the composite resin material are computed. However, to reduce a calculation load, the filler dispersion degree Vwf may be substituted into the input terms of (Equation 1) to (Equation 14) as a constant value in a plurality of calculation processes, and calculation processing of computing the exothermic reaction speed and the physical property of the composite resin material may be executed for each calculation process $t_n$.

In addition, calculation equations for the exothermic reaction speed, the viscosity, the density, the specific heat, and the thermal conductivity are not limited to the above (Equation 1) to (Equation 14). These values may be computed using an arbitrary equation as long as the equation includes an input term of the filler dispersion degree Vwf.

In addition, for example, it is possible to analyze one or a plurality of types of the density, the specific heat, and the thermal conductivity as constant values. In addition, to reduce a calculation load, a smaller value than an actual value may be input as an initial filler filling degree Vwf in step 1004, a filler filling degree in each calculation process $t_n$ may be computed in step 1007, and then the exothermic reaction speed or the physical property such as the viscosity of the composite resin material 1 may be computed using a value obtained by correcting the filler filling degree Vwf computed in latest step 1007 in step 1006 of a subsequent calculation process $t_{n+1}$.

According to the flow analysis method described above, when the exothermic reaction speed is computed using the exothermic reaction speed equations (Equation 1) to (Equation 8) including the filler dispersion degree as an input term, and a predicted value of the flow velocity or the temperature of the composite resin material is computed using this computed value, it is possible to obtain a more accurate analysis result with respect to a flow state of the composite resin material when compared to a conventional flow analysis method using a formula not including a filler dispersion degree as an input term.

In particular, when the viscosity in each calculation process is computed using the viscosity equations (Equation 9) to (Equation 11) having the filler dispersion degree as a change factor, it is possible to trace sequential fluctuations in the viscosity state of the composite resin material by reflecting a change in the filler dispersion degree. When the viscosity computed in this way is used for computation of the predicted value of the flow velocity or the temperature of the composite resin material, it is possible to obtain a more accurate analysis result with respect to the flow state of the composite resin material.

In addition, similarly, with respect to the density, the specific heat, and the thermal conductivity, when these physical properties are computed using the density equation (Equation 12), the specific heat equation (Equation 13), and the thermal conductivity equation (Equation 14) including the filler dispersion degree as an input term, and computed values thereof are used for computation of the predicted value of the flow velocity or the temperature of the composite resin material, a change in the filler dispersion degree is reflected in the physical property such as the density, and thus it is possible to obtain a more accurate analysis result with respect to a flow state of the composite resin material.

According to the flow analysis method described above, it is possible to optimize conditions with respect to a molding process condition such as an initial velocity or a mold temperature of the composite resin material, a package structure such as an element dimension or a dimension of a filled region of the composite resin material, a filler shape, a filler dimension, an initial filler dispersion degree, and a physical property of the composite resin material such as a physical property of a resin component. For this reason, without prototyping the product, it is possible to predict optimum conditions, and it is possible to reduce cost and shorten a development period.

ANALYSIS EXAMPLE

Next, an example of flow analysis when the space 17 is filled with the composite resin material 1 by the transfer molding method described in FIG. 1 will be described below. The following flow analysis was carried out according to the flowchart illustrated in FIG. 5.

Figure 7:
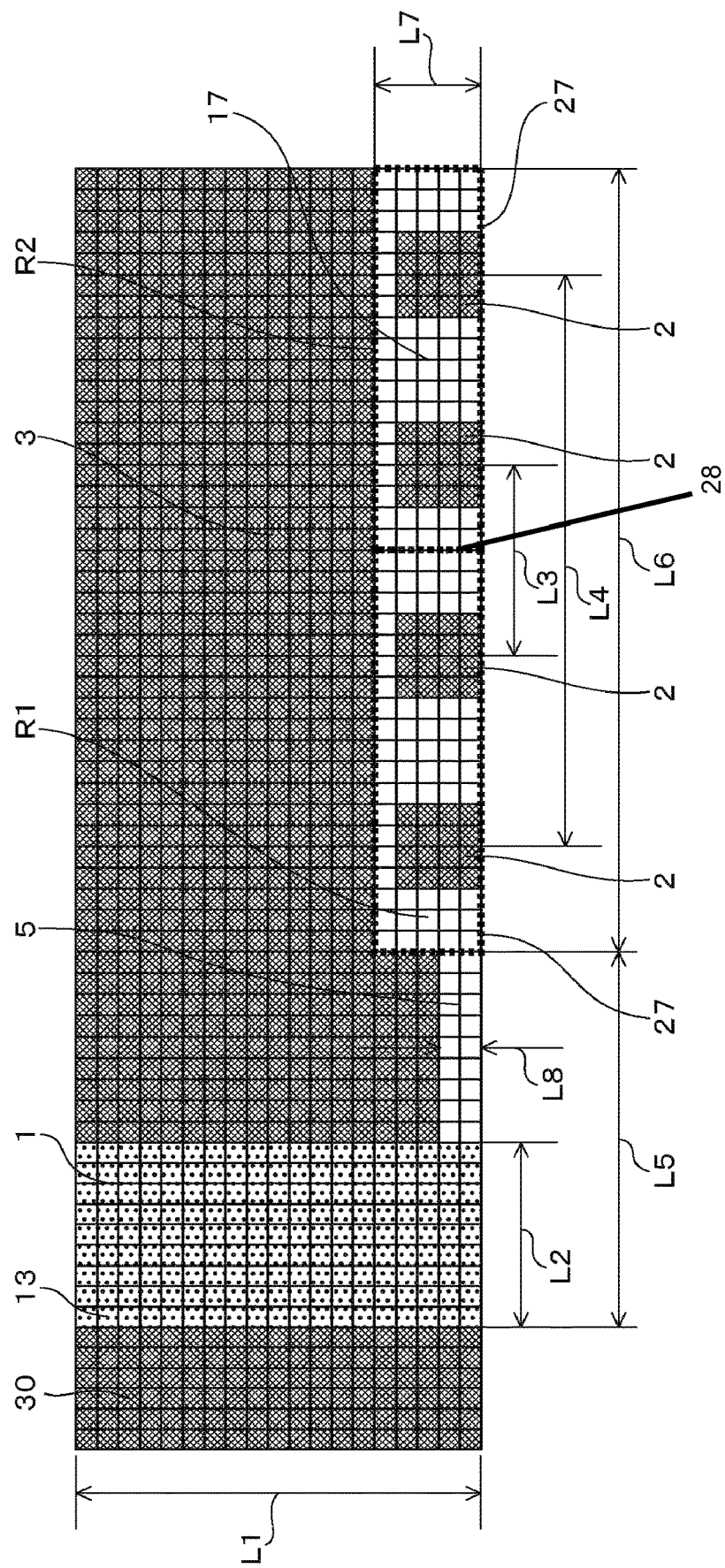
FIG. 7 is a diagram illustrating analysis target models of Analysis Examples 1 to 3.

FIG. 7 illustrates a shape of an analysis target model created in step 1001 before start of analysis. The shape data of the finite element created in step 1002 is indicated by an element division line 28 in FIG. 7. Four semiconductor chips 2 were disposed in the space 17 between the upper mold 3 and the lower mold 4. The divided regions were set to two regions of R1 and R2 surrounded by a region division line 27 indicated by a dotted line in FIG. 7. Each of the divided regions R1 and R2 was set to include two of the semiconductor chips 2. In the analysis target model illustrated in FIG. 7, the composite resin material 1 initially disposed in the mold 3 is caused to flow into the space 17 of the mold from the gate/cull portion 5 by moving a plunger 30 disposed at a left end of FIG. 7 toward a right side in FIG. 7.

In FIG. 7, L1 was set to 10 mm, L2 was set to 5 mm, L3 was set to 5 mm, L4 was set to 17 mm, L5 was set to 10 mm, L6 was set to 20 mm, L7 was set to 2.5 mm, and L8 was set to 1.0 mm. The dimensions of each of the semiconductor chips 2 were set to 2 mm×2 mm.

First, in step 1004, the eigenvalue specified by the type of the composite resin material or the constituent material thereof in the exothermic reaction speed equations (Equation 1) to (Equation 8), the viscosity equations (Equation 9) to (Equation 11), the density equation (Equation 12), the specific heat equation (Equation 13), and the thermal conductivity equation (Equation 14) is input to the storage device 25 by the input device (not illustrated). Here, values shown in Table 2 (see FIG. 12) were used as coefficients of the exothermic reaction speed equations, and values shown in Table 3 (see FIG. 13) were used as coefficients of the viscosity equations. In addition, values shown in Table 1 (see FIG. 11) were used as the thermal conductivities, the linear expansion coefficients, and the densities of the resin 29 and the filler 13, respectively. In addition, the initial filler dispersion degree was set to 0.7 (70 wt %). In addition, a filler having a spherical shape and a diameter of 50 μm was used as the filler.

Under the above-mentioned conditions, processes of steps 1006, 1007, 1008, and 1009 were executed (Analysis Examples 1 to 3) with respect to a condition (Condition Example 1) in which a divided region is not set for a range for executing calculation of (Equation 1) to (Equation 14) having the filler dispersion degree Vwf as an input term and conditions (Condition Examples 2 and 3) in which a divided region is set to a range for executing calculation of (Equation 1) to (Equation 14) having the filler dispersion degree Vwf as an input term, respectively.

The boundary condition and the molding condition, which are input terms in step 1005, were set to conditions shown in Conditions 1 to 3 below. In Analysis Examples 1 to 3, a time of an initial calculation step $t_1$ was set to 0.00001 s, and an upper limit of an apparatus pressure applied to the plunger 30 was set to 12 MPa.

Condition 1: An initial temperature 170° C. of the composite resin material 1, a mold temperature and a temperature of a boundary region 170° C. (constant), and an initial velocity $7.1 \times 10^{-4}$ (m/s) of the plunger 30 to the right side were input as the boundary condition/molding condition of step 1005. An initial velocity of the composite resin material 1 is obtained by an initial velocity of the plunger 30. This description is applied to Conditions 2 and 3 below.

The temperature of the boundary region corresponds to a temperature of a boundary between an analysis target region and an external region and corresponds to a temperature of a contact portion with respect to a boundary with the composite resin material 1 when the composite resin material 1 flows and reaches this boundary. In addition, in Analysis Example 1, there is no setting of a divided region for a range for executing calculation of (Equation 1) to (Equation 14) having the filler dispersion degree Vwf as an input term, and a single region is set as a calculation target region.

Condition 2: An initial temperature 170° C. of the composite resin material 1, a mold temperature and a temperature of a boundary region 170° C. (constant), and an initial velocity $7.1 \times 10^{-4}$ (m/s) of the plunger 30 to the right side were input as the boundary condition/molding condition of step 1005.

In addition, two divided regions corresponding to the divided region R1 and the divided region R2 were set for a range for executing calculation of (Equation 1) to (Equation 14) having the filler dispersion degree Vwf as an input term (see FIG. 7).

Condition 3: An initial temperature 160° C. of the composite resin material 1, a mold temperature and a temperature of a boundary region 160° C. (constant), and an initial velocity $7.1 \times 10^{-4}$ (m/s) of the plunger 30 to the right side were input as the boundary condition/molding condition of step 1005.

In addition, two divided regions corresponding to the divided region R1 and the divided region R2 were set for a range for executing calculation of (Equation 1) to (Equation 14) having the filler dispersion degree Vwf as an input term (see FIG. 7).

In addition, in Analysis Examples 1 to 3, a velocity condition of the plunger 30 was fixed at the initial velocity even when an analysis time has elapsed. However, when the pressure for realizing the initial velocity of the plunger 30 exceeds the upper limit pressure (12 MPa) of the apparatus, the velocity condition of the plunger 30 was set to be smaller than the initial velocity to execute calculation processing. When the filler 13 comes into contact with the boundary between the analysis target region and the external region, the mold wall surface, and the component, the filler 13 was set to adhere to the boundary, the mold wall surface, and the component.

Analysis Example 1

In Analysis Example 1, a conventional general analysis was conducted such that an initial filler dispersion degree (Vwf=0.7; constant value) was input to the input term of the filler dispersion degree Vwf of (Equation 1) to (Equation 14) with respect to all the regions to be analyzed in any calculation process of step 1006, and calculation processing of step 1007 was performed using an obtained exothermic reaction speed or physical property such as viscosity. That is, in Analysis Example 1, computation of the filler dispersion degree in step 1007 was not performed.

Figure 8:
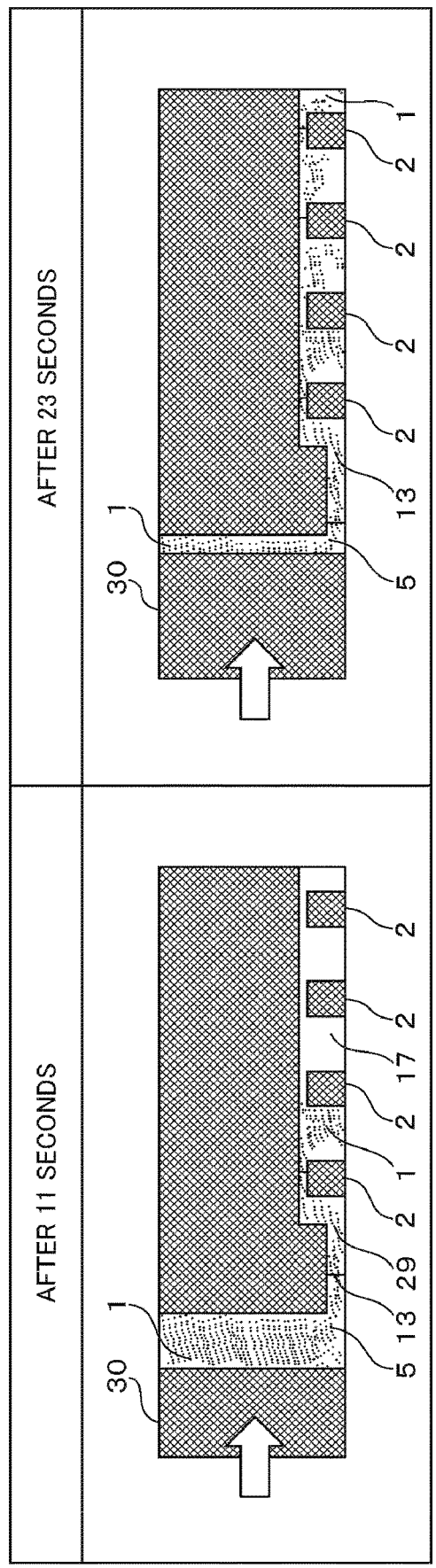
FIG. 8 is a diagram illustrating an analysis result of a flow state of the composite resin material 1 in Analysis Example 1.

FIG. 8 illustrates an analysis result of the filling state associated with the flow of the composite resin material 1 in Analysis Example 1 using Condition 1. FIG. 8 illustrates analysis results after 11 seconds and 23 seconds from the start of analysis in step 1007.

As illustrated in FIG. 8, by the plunger 30 moving to the right side of FIG. 8, the composite resin material 1 initially disposed in the mold flowed into the space 17 in the mold by passing through the gate/cull portion 5. After 23 seconds, as a result, there was no unfilled region, and the entire space 17 in the mold was filled with the composite resin material 1. In this instance, a pressure (filling pressure) necessary for filling was calculated to be 400 Pa. As a calculation result, this pressure was a sufficiently low value when compared to 12 MPa corresponding to the upper limit of the apparatus pressure, and filling can be performed without exceeding an upper limit of the apparatus.

Analysis Example 2

In Analysis Example 2, in step 1007, the filler dispersion degree Vwf of each of the divided region R1 and the divided region R2 in each calculation process was computed, and the computed value of the filler dispersion degree Vwf was substituted into the input term Vwf of the filler dispersion degree of (Equation 1) to (Equation 14) in step 1006 of a subsequent calculation process to compute the exothermic reaction speed or the physical property such as the viscosity. Calculation processing of (Equation 15) to (Equation 19) was performed using this computed value. This description is applied to Condition 3. In Analysis Example 2, at the calculation end time, the filler dispersion degree Vwf of the divided region R1 was computed to be 0.85, and the filler dispersion degree Vwf of the divided region R2 was computed to be 0.55.

Figure 9:
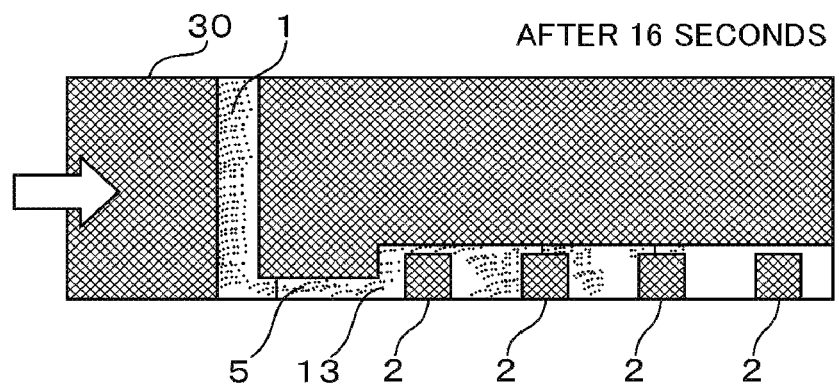
FIG. 9 is a diagram illustrating an analysis result of a flow state of the composite resin material 1 in Analysis Example 2.

FIG. 9 illustrates an analysis result of the filling state associated with the flow of the composite resin material 1 in Analysis Example 2 using Condition 2. FIG. 9 illustrates an analysis result after 16 seconds from the start of analysis in step 1007. In Analysis Example 2, as a calculation result, at a time point 16 seconds after the start of the analysis, the apparatus pressure (filling pressure) required for moving the plunger 30 reached 12 MPa corresponding to the upper limit of the apparatus pressure, and resin was not allowed to further flow into the space 17.

Analysis Example 3

In Analysis Example 3, flow analysis was conducted similarly to Analysis Example 2 except that Condition 3 was used for a velocity condition and a temperature condition. In Analysis Example 3, at the calculation end time, the filler dispersion degree Vwf of the divided region 1 was computed to be 0.85, and the filler dispersion degree Vwf of the divided region 2 was computed to be 0.55.

Figure 10:
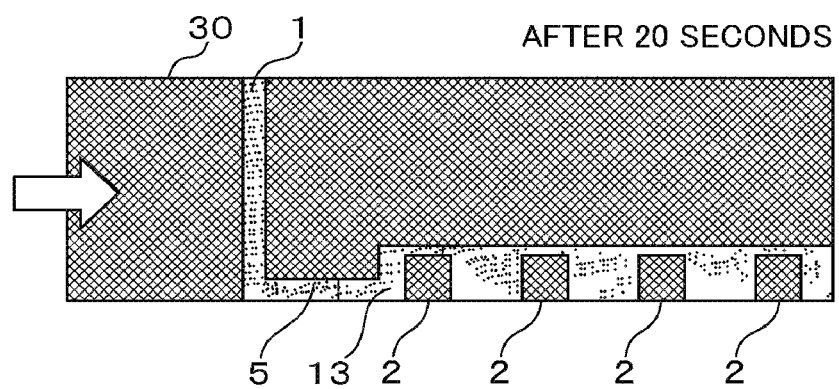
FIG. 10 is a diagram illustrating an analysis result of a flow state of the composite resin material 1 in Analysis Example 3.

FIG. 10 illustrates an analysis result of the filling state associated with the flow of the composite resin material 1 in Analysis Example 3 using Condition 3. FIG. 10 illustrates an analysis result after 20 seconds from the start of analysis in step 1007. In Analysis Example 3, a pressure (filling pressure) required for filling was computed to be 1.1 MPa. As illustrated in FIG. 10, in Analysis Example 3, as an analysis result, at a pressure (1.1 MPa) less than or equal to 12 MPa corresponding to the upper limit of the apparatus pressure, the divided region R1 and the divided region R2 of the space 17 were filled with the composite resin material 1.

In the example described above, a description has been given of a case in which a spherical filler is mainly used as the filler 13 contained in the composite resin material 1. However, the filler is not limited to the spherical filler. For example, the flow analysis method according to the embodiment can be applied to a composite resin material using a filler having an arbitrary shape including a bar shape, a flake shape, a polygonal shape, an elliptical sphere shape, etc.

In addition, in the example described above, a description has been given of the flow analysis method for the composite resin material 1 that polymerizes or crosslinks due to heat generation. However, the invention is not limited thereto. For example, the flow analysis method according to the embodiment can be applied to flow analysis of a liquid that contains a filler and flows due to heat generation.

For example, the flow analyzing method described above may be applied to analysis of a flow state such as a flow velocity or a temperature during filling of a composite resin material when an electronic component such as a semiconductor package is integrally molded by a resin molding method such as transfer molding or compression molding.

REFERENCE SIGNS LIST

1 Composite resin material
2 Element
3 Upper mold
4 Lower mold
5 Gate/cull portion
6 Gold wire
8 Lead frame
9 Fixing film
11 Rewiring layer
12 Solder ball
13 Filler
17 Space
23 Display device
24 Calculation device
25 Storage device
26 LAN
27 Region division line
28 Element division line
29 Resin
30 Plunger
$R_{MN}$ Region subjected to calculation
R1, R2, R11 to 14, R21 to 24, R31 to 34, R41 to 44 Divided region

The invention claimed is:

1. A flow analysis method for a composite resin material having a filler and a resin, the flow analysis method comprising:
identifying a region in which the composite resin material flows;
dividing the region into a plurality of divided regions;
calculating a first exothermic reaction speed of the composite resin material in the region using an initial filler dispersion degree in the composite resin material in some of the plurality of divided regions;
calculating a temperature and a second filler dispersion degree of the composite resin material in the region using the first exothermic reaction speed in the some of the plurality of divided regions;
calculating a second exothermic reaction speed in a process subsequent to a certain process for flow analysis using the calculated second filler dispersion degree in the process for flow analysis in some of the plurality of divided regions;
determining if an elapsed time is less than a predetermined time, and when the elapsed time is less than the predetermined time
recalculate and update the first exothermic reaction speed of the composite resin material in the region using the calculated second filler dispersion degree in the composite resin material in additional of the plurality of divided regions,
recalculate and update the temperature and the second filler dispersion degree of the composite resin material in the region using the updated first exothermic reaction speed in the additional of the plurality of divided regions, and
recalculate and update the second exothermic reaction speed in a process subsequent to a certain process for flow analysis using the updated second filler dispersion degree in the process for flow analysis in the additional of the plurality of divided regions; and
changing a velocity of a plunger based on the second exothermic reaction speed calculated.

2. The flow analysis method according to claim 1, wherein a filler dispersion degree computed in a certain divided region of the plurality of divided regions is used for computation of an exothermic reaction speed in an other divided region.

3. The flow analysis method according to claim 1, wherein the process continues until the exothermic reaction speed of the composite resin material is calculated using the filler dispersion degree in the composite resin material, and the temperature and the filler dispersion degree of the composite resin material in the region are calculated using the calculated first exothermic reaction speed.

4. The flow analysis method according to claim 1, wherein a flow velocity of the composite resin material in the region in the process is calculated using the calculated first exothermic reaction speed.

5. The flow analysis method according to claim 1,
wherein a viscosity of the composite resin material in the process is calculated using a viscosity equation having the temperature of the composite resin material as a variable,
the temperature and the filler dispersion degree of the composite resin material in the region is computed using the calculated viscosity of the composite resin material in addition to the first exothermic reaction speed, and
a viscosity of the composite resin material in a process subsequent to the process is computed by substituting the calculated temperature of the composite resin material into the viscosity equation.

6. The flow analysis method according to claim 5, wherein an equation having a reaction rate as a variable is used as the viscosity equation, the reaction rate being calculated by a calculation equation of an exothermic reaction speed having a filler dispersion degree as a variable.

7. The flow analysis method according to claim 5, wherein each of a flow velocity of the resin and a flow velocity of the filler is computed using the viscosity equation, and a filler dispersion degree of the composite resin material in the region in the process is computed using the calculated flow velocity of the resin and the calculated flow velocity of the filler.

8. The flow analysis method according to claim 5,
wherein a density of the composite resin material in the process is computed using a density equation having the filler dispersion degree in the composite resin material as a variable,
the filler dispersion degree in the region is calculated using the calculated density of the composite resin material in addition to the viscosity of the composite resin material, and
a density of the composite resin material in a process subsequent to the process is calculated by substituting the computed filler dispersion degree of the composite resin material into the density equation.

9. The flow analysis method according to claim 5,
wherein a thermal conductivity of the composite resin material in the process is computed using a thermal conductivity equation having the filler dispersion degree in the composite resin material as a variable,
the filler dispersion degree in the region is computed using the calculated thermal conductivity of the composite resin material in addition to the viscosity of the composite resin material, and a thermal conductivity of the composite resin material in a process subsequent to the process is calculated by substituting the computed filler dispersion degree of the composite resin material into the thermal conductivity equation.

10. The flow analysis method according to claim 5,
wherein a specific heat of the composite resin material in the process is calculated using a specific heat equation having the filler dispersion degree in the composite resin material as a variable,
the filler dispersion degree in the region is calculated using the computed specific heat of the composite resin material in addition to the viscosity of the composite resin material, and
a specific heat of the composite resin material in a process subsequent to the process is computed by substituting the calculated filler dispersion degree of the composite resin material into the specific heat equation.

11. The flow analysis method according to claim 5,
wherein a density, a thermal conductivity, and a specific heat of the composite resin material in the process are calculated using a density equation having the filler dispersion degree in the composite resin material as a variable, a thermal conductivity equation having the filler dispersion degree in the composite resin material as a variable, and a specific heat equation having the filler dispersion degree in the composite resin material as a variable,
the temperature and the filler dispersion degree of the composite resin material in the region are calculated using the computed density, specific heat, and thermal conductivity of the composite resin material in addition to the viscosity of the composite resin material, and
a density, a specific heat, and a thermal conductivity of the composite resin material in a process subsequent to the process are calculated by substituting the computed filler dispersion degree of the composite resin material into each of the density equation, the specific heat equation, and the thermal conductivity equation.

12. A flow analysis system for performing flow analysis of a composite resin material having a filler and a resin, the flow analysis system comprising:
a processor that
identifies a region in which the composite resin material flows,
divides the region into a plurality of divided regions,
calculates a first exothermic reaction speed of the composite resin material using an initial filler dispersion degree in some of the plurality of divided regions,
calculates a temperature, a second filler dispersion degree, and a flow velocity of the composite resin material using the first exothermic reaction speed in the some of the plurality of divided regions,
calculates a second exothermic reaction speed in a process subsequent to a process for flow analysis using the calculated second filler dispersion degree and the temperature in the process for flow analysis in the some of the plurality of divided regions,
determines if an elapsed time is less than a predetermined time, and when the elapsed time is less than the predetermined time
recalculates and updates the first exothermic reaction speed of the composite resin material in the region using the calculated second filler dispersion degree in the composite resin material in additional of the plurality of divided regions,
recalculates and updates the temperature and the second filler dispersion degree of the composite resin material in the region using the updated first exothermic reaction speed in the additional of the plurality of divided regions, and
recalculates and updates the second exothermic reaction speed in a process subsequent to a certain process for flow analysis using the updated second filler dispersion degree in the process for flow analysis in the additional of the plurality of divided regions, and
changes a velocity of a plunger based on the second exothermic reaction speed calculated;
a memory that stores data related to the temperature and the filler dispersion degree of the composite resin material calculated by the processor; and
a display device that displays data related to the flow velocity of the composite resin material calculated by the processor.

13. The flow analysis method according to claim 1, wherein
the some of the plurality of divided regions is an amount of the plurality of divided regions that is less than the additional of the plurality of divided regions, and
the some of the plurality of divided regions contain different regions than the additional of the plurality of divided regions.

* * * * *